United States Patent
Yonezawa (10) Patent No.: US 9,861,561 B2
(45) Date of Patent: Jan. 9, 2018

(54) AQUEOUS COMPOSITION

(71) Applicant: SHISEIDO COMPANY, LTD., Chuo-ku, Tokyo (JP)

(72) Inventor: Tetsuro Yonezawa, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 14/785,880

(22) PCT Filed: Feb. 3, 2014

(86) PCT No.: PCT/JP2014/052449
§ 371 (c)(1),
(2) Date: Oct. 21, 2015

(87) PCT Pub. No.: WO2014/174868
PCT Pub. Date: Oct. 30, 2014

(65) Prior Publication Data
US 2016/0058679 A1    Mar. 3, 2016

(30) Foreign Application Priority Data

Apr. 26, 2013 (JP) .................. 2013-094214

(51) Int. Cl.
| | | |
|---|---|---|
| A61K 8/06 | (2006.01) | |
| A61K 8/14 | (2006.01) | |
| A61Q 19/00 | (2006.01) | |
| A61K 8/92 | (2006.01) | |
| A61K 8/31 | (2006.01) | |
| A61K 8/44 | (2006.01) | |
| A61K 8/60 | (2006.01) | |
| A61K 8/86 | (2006.01) | |
| A61K 8/894 | (2006.01) | |
| A61K 8/03 | (2006.01) | |
| A61K 8/55 | (2006.01) | |

(52) U.S. Cl.
CPC ............... *A61K 8/14* (2013.01); *A61K 8/03* (2013.01); *A61K 8/062* (2013.01); *A61K 8/31* (2013.01); *A61K 8/44* (2013.01); *A61K 8/553* (2013.01); *A61K 8/60* (2013.01); *A61K 8/86* (2013.01); *A61K 8/894* (2013.01); *A61K 8/922* (2013.01); *A61Q 19/00* (2013.01); *A61K 2800/592* (2013.01)

(58) Field of Classification Search
CPC . A61Q 19/00; A61K 8/03; A61K 8/06; A61K 8/062; A61K 8/14; A61K 8/31; A61K 8/44; A61K 8/86
See application file for complete search history.

(56) References Cited

U.S. PATENT DOCUMENTS

| | | | |
|---|---|---|---|
| 5,364,633 A | 11/1994 | Hill et al. | |
| 8,105,996 B2* | 1/2012 | Wei ................. | A61K 8/044 510/121 |
| 2010/0080832 A1* | 4/2010 | Watanabe ............... | A61K 8/14 424/401 |
| 2010/0215703 A1 | 8/2010 | Watanabe et al. | |
| 2011/0236447 A1* | 9/2011 | Yoshimura ............. | A61K 8/06 424/401 |
| 2012/0183480 A1 | 7/2012 | Nagare et al. | |

FOREIGN PATENT DOCUMENTS

| | | |
|---|---|---|
| DE | 0 92 16 886.8 | 5/1994 |
| EP | 2 149 362 | 2/2010 |
| EP | 2 561 862 | 2/2013 |
| JP | H06-279241 | 4/1994 |
| JP | 2004-010517 | 1/2004 |
| JP | 2007-277192 | 10/2007 |
| JP | 2011-241175 | 12/2011 |
| JP | 2012-092084 | 5/2012 |
| JP | 2012-158591 | 8/2012 |
| WO | WO 2008/143140 | 11/2008 |
| WO | WO 2010/064678 | 6/2010 |

OTHER PUBLICATIONS

Serial No. PCT/JP2014/052449 dated Apr. 22, 2014, International Search Report ISR (2-pages in Japanese) and English Language Translation (2-pages.
JP 2013-094214 $1^{st}$ Office Action dated Apr. 22, 2014; 4 pages Japanese, 4 pages English and certificate of translation.
JP 2013-094214 Response to Office Action dated Jun. 16, 2014, 10 pages English, 6 pages—Japanese, and certificate of translation.
JP 2013-094214, Notice of Allowance dated Jan. 23, 2015, 3 pages—English, 3 pages—Japanese and certificate of translation.
JP 2013-94214, JP Granted JP5690373B2, Published JP Patent with claims as issued (underlins shown), and Translation pg. claims issued and certificate of translation (26 pages, 5 in English).
"Shin Etsu-Silicon-Reactive & Non-Reactive Modified Silicone Fluid", Jan. 1, 2006, 10 pages—English, http://www.silicone.jp/, Silicon Division, Sales and Marketing Dept. 1 (Fluids), Shin-Etsu Silicons of America, Inc.
Ep 14787501.7, Extended European Search Report, dated Oct. 10, 2016, 9 pages—English.

\* cited by examiner

*Primary Examiner* — Mina Haghighatian
(74) *Attorney, Agent, or Firm* — Andrew F. Young, Esq.; Lackenbach Siegel, LLP (57) ABSTRACT

The present invention provides an aqueous composition in which vesicles and oil drops are stably coexistent.
The aqueous composition of the present invention is characterized by containing
(a) an amphiphilic compound,
(b) water, and
(c) oil,
wherein vesicles formed with component (a) and oil drops containing component (c) are present in component (b).

17 Claims, 3 Drawing Sheets

AQUEOUS COMPOSITION

RELATED APPLICATIONS

This application relates to and claims priority from Ser. No.: PCT/JP2014/052449 filed Feb. 3, 2014 which claims the priority of Japanese Patent Application No. 2013-94214 filed on Apr. 26, 2013, the entire contents of each of which are incorporated herein by reference.

FIELD OF THE INVENTION

The present invention relates to an aqueous composition, and in particular, relates to an aqueous composition containing vesicles and oil drops.

BACKGROUND OF THE INVENTION

Some of amphiphilic compounds having both hydrophilicity and hydrophobicity form a bilayer membrane (lamellar phase) spherical structure in an aqueous phase. Such a small sphere having the bilayer membrane structure is called a liposome or a vesicle that can stably incorporate an aqueous component inside the small sphere and oil in the spherical membrane.

Silicone surfactants (for example, refer to Patent Literature 1) and phospholipids (for example, refer to Patent Literature 2) have been reported as amphiphilic compounds that can form such vesicles.

However, a large amount of oil could not be blended in the aqueous composition containing vesicles. That is, even when the inclusion of a large amount of oil into such a system is attempted, the emulsification takes place and the formation of vesicles is not feasible. Accordingly, the blending of only the amount of oil that can be contained inside the vesicle membrane has thus far been investigated for aqueous composition containing vesicles. Thus, the blending quantity of oil was small in the aqueous composition containing vesicles so that the provision of moistness was difficult even though the fresh feeling was excellent, On the other hand, an emulsion composition in which a sufficient amount of oil can be blended was not up to the aqueous composition containing vesicles in terms of compatibility and non-stickiness.

PATENT DOCUMENT

Patent literature 1: Japanese unexamined patent publication No. H07-323222
Patent literature 2: Japanese unexamined patent publication No. 2007-277192

DISCLOSURE OF THE INVENTION

Problem to be Solved by the Invention

The present invention was made in view of the above-described problems of the conventional art, and an object is to provide an aqueous composition wherein vesicles and oil drops are stably coexistent.

Means to Solve the Problem

The present inventor and associates have diligently studied to solve the above-described problems and, as a result, found that an aqueous composition containing vesicles and oil drops, providing excellent skin compatibility and moist feeling, etc., can be obtained by containing an amphiphilic compound (a), water (b), and oil (c); and preferably containing specific oil; and then completed the present invention, accordingly.

That is, the aqueous composition of the present invention comprises;
(a) an amphiphilic compound,
(b) water, and
(c) oil,
wherein component (b) comprises vesicles that component (a) forms and oil drops containing component (c).

In the above-described aqueous composition, it is preferable that that component (a) comprises the amphoteric compound capable of forming a vesicle.

In the above-described aqueous composition, it is preferable that component (a) is selected from the group consisting of sugar fatty acid ester, polyoxyethylene hydrogenated castor oil derivative, acyl-amino acid metal salt, phospholipid, and silicone surfactant having HLB of 4 to 12.

In the above-described aqueous composition, it is preferable that component (c) contains the oil separate from an amphiphilic compound (a) when mixed therewith. In the above-described aqueous composition, it is preferable that component (a) comprises a silicone surfactant having HLB of 4 to 12 and component (c) comprises hydrocarbon oil. In the above-described aqueous composition, it is preferable that component (a) comprises an anionic surfactant and/or a silicone surfactant having HLB of more than 12.

In the above-described aqueous composition, it is preferable that component (b) comprises vesicles formed from a silicone surfactant having HLB of 4 to 12 and oil drops comprising hydrocarbon oil, and wherein an anionic surfactant and/or a silicone surfactant having HLB of more than 12 adheres on the surface of the vesicles.

In the above-described aqueous composition, it is preferable that component (c) comprise a silicone oil and/or a polar oil having IOB of 0.05 to 0.8.

In the above-described aqueous composition, it is preferable that component (b) comprises vesicles formed from a silicone surfactant having HLB of 4 to 12 and oil drops comprising hydrocarbon oil and that the bimolecular membrane of the vesicles comprises a silicone oil and/or a polar oil having IOB of 0.05 to 0.8.

The aqueous composition of the present invention is characterized in that after an aqueous solution containing vesicles comprising an amphiphilic compound (a) is obtained by mixing component (a) and water (b), the aqueous composition is obtained by mixing the obtained aqueous solution and oil (c).

In addition, the production method of the aqueous composition of the present invention is characterized by having a step of preparing an aqueous solution comprising vesicles that comprises component (a) by mixing an amphiphilic compound (a) and water (b), and a step of mixing the aqueous solution and oil (c).

In addition, the production method of the aqueous composition of the present invention is characterized by having a step of preparing an aqueous solution containing vesicles comprising component (a) by mixing (a) a silicone surfactant having HLB of 4 to 12 and water (b), and a step of mixing the aqueous solution and hydrocarbon oil (c).

In the above-described production method, it is preferable to add a silicone oil and/or a polar oil having IOB of 0.05 to 0.8 when component (a) and component (b) are mixed.

In addition, the double-layered composition of the present invention is characterized in that the double-layered composition contains an amphiphilic compound (a), water (b) and oil (c), and that an aqueous layer comprising vesicles formed from component (a) are present in component (b), and an oil layer containing component (c).

In the above-described double-layered composition, it is preferable that a vesicle-formable amphiphilic compound is contained in component (a).

In the above-described double-layered composition, it is preferable that component (a) is selected from the group consisting of sugar fatty acid ester, polyoxyethylene hydrogenated castor oil derivative, acyl-amino acid metal salt, phospholipid, and silicone surfactant having HLB of 4 to 12.

In the above-described double-layered composition, it is preferable that oil that separate, when mixed with an amphiphilic compound (a), is contained as component (c).

In the above-described double-layered composition, it is preferable that a silicone surfactant having HLB of 4 to 12 is contained in component (a) and hydrocarbon oil is contained in component (c).

In the above-described double-layered composition, it is preferable that an anionic surfactant and/or a silicone surfactant having HLB of more than 12 is contained in component (a).

In the above-described double-layered composition, it is preferable that it comprises an aqueous layer, wherein vesicles formed from a silicone surfactant having HLB of 4 to 12 are present, and an oil layer containing hydrocarbon oil, and an anionic surfactant and/or a silicone surfactant having HLB of more than 12 adheres on the surface of the vesicles.

In the above-described double-layered composition, it is preferable that a silicone oil and/or a polar oil having IOB of 0.05 to 0.8 is contained in component (c).

In the above-described double-layered composition, it is preferable that it comprises an aqueous layer, wherein vesicles formed with a silicone surfactant having HLB of 4 to 12 are present, and an oil layer containing hydrocarbon oil, and a silicone oil and/or a polar oil having IOB of 0.05 to 0.8 is contained in the bimolecular membrane of the vesicles.

In the above-described double-layered composition, it is preferable that sodium chloride is contained in component (b).

Effect of the Invention

The present invention provides an aqueous composition containing vesicles and oil drops. The aqueous composition of the present invention has good compatibility when applied on the skin.

BEST MODE FOR CARRYING OUT THE INVENTION

The aqueous composition of the present invention is characterized by containing
(a) an amphiphilic compound,
(b) water, and
(c) oil,
wherein vesicles formed from component (a) and oil drops containing component (c) are present in component (b).

Figure 1:
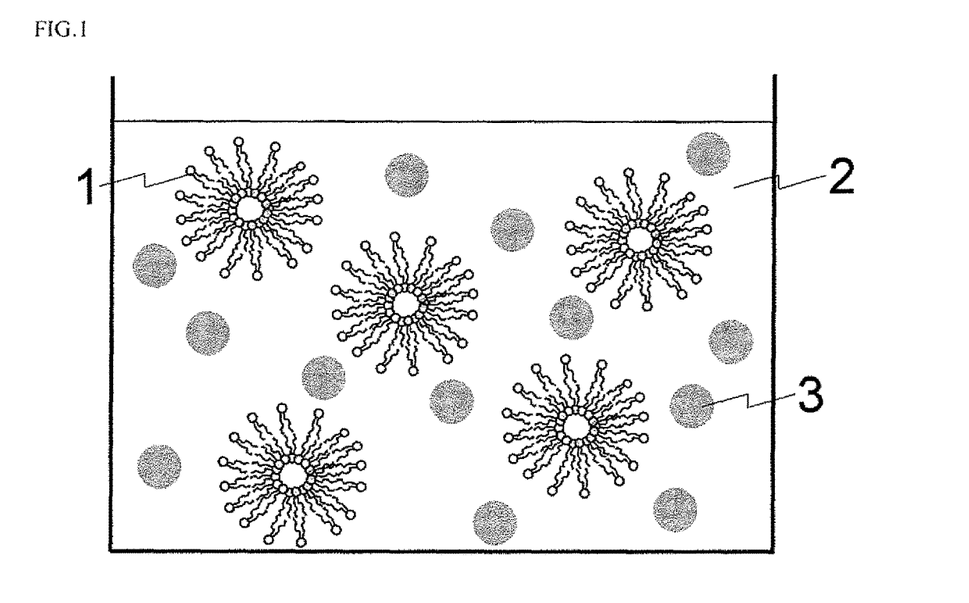
FIG. 1 shows the aqueous composition of the present invention.

That is, the aqueous composition of the present invention is a composition shown in FIG. 1. In the composition of the present invention, vesicles formed from component (a) and oil drops containing component (c) are present in component (b). The composition of the present invention can be prepared by a publicly known method by which the vesicle-containing composition can be obtained.

((a) Amphiphilic Compound)

The amphiphilic compounds must include an amphiphilic compound capable of forming a vesicle, i.e., vesicle-formable amphiphilic compound.

The vesicle-formable amphiphilic compounds may include, e.g., sugar fatty acid ester, polyoxyethylene hydrogenated castor oil derivative, acyl-amino acid metal salt, phospholipid, silicone surfactant having HLB of 4 to 12, and so forth but not limited in particular.

Sugar fatty acid esters may include, e.g., sucrose fatty acid ester, maltitol fatty acid ester and trehalose fatty acid ester, but not limited in particular.

The number of hydroxyl groups substituted by a fatty acid (degree of esterification) is not limited in particular, but preferably monoester, diester and triester, more preferably monoester and diester, and most preferably monoester.

The constituent fatty acid of sugar fatty acid ester is preferably a saturated or unsaturated fatty acid having 12 to 22 carbon atoms, either linear or branched chain.

The fatty acid may include lauric acid, myristic acid, palmitic acid, stearic acid, isostearic acid, arachic acid, behenic acid, tetradecene acid, hexadecane acid, octadecene acid, octadecadiene acid, eicosenoic acid, eicosatetraenoic acid, docosenoic acid, and octadecatrienoic acid, but not limited. Among them, stearic acid is preferable.

In the case of a diester, two fatty acids may be different.

As polyoxyethylene hydrogenated castor oil derivative, the compound having the below formula (1) is preferably used.

[Compound 1]

$$\begin{aligned}
&CH_2-O-(CH_2CH_2O)_L-\overset{O}{\overset{\|}{C}}-(CH_2)_{10}\overset{O-(CH_2CH_2O)_XH}{\overset{|}{CH}}(CH_2)_5CH_3 \\
&CH_2-O-(CH_2CH_2O)_M-\overset{O}{\overset{\|}{C}}-(CH_2)_{10}\overset{O-(CH_2CH_2O)_YH}{\overset{|}{CH}}(CH_2)_5CH_3 \\
&CH_2-O-(CH_2CH_2O)_N-\overset{O}{\overset{\|}{C}}-(CH_2)_{10}\overset{O-(CH_2CH_2O)_ZH}{\overset{|}{CH}}(CH_2)_5CH_3
\end{aligned} \quad (1)$$

In the above formula (1), the sum of L+M+N+X+Y+Z that represents the average addition molar number (E) of ethylene oxides is $10 \leq E \leq 20$.

As the acyl-amino acid metal salt, a metal salt of acyl-amino acid having 12 to 22 carbon atoms is preferable.

Such acyl-amino acid metal salts include, e.g., sodium N-lauroyl-L-glutamate, N-stearoyl-L-glutamate, and sodium di-(N-lauroylglutamyl) lysine.

Phospholipids include, e.g., egg yolk phospholipid, soybean phospholipid, and hydrogenated materials thereof, and sphingophospholipids such as sphingomyelin.

The silicone surfactant having HLB of 4 to 12 is not limited in particular and include, e.g., polyoxyalkylene-modified silicones, etc.

As the vesicle-formable amphiphilic compound, the silicone surfactant having HLB of 4 to 12 shown in the below-described formula (2) is preferably used.

[Compound 2]

In the above-described formula (2), $R^1$ is a hydrogen atom or an alkyl group having 1 to 6 carbon atoms. As for A, at least one of them is a polyoxyalkylene group represented by the formula: $—(CH_2)_a—(C_2H_4O)_b—(C_3H_6O)_c—R^2$ (in the formula, $R^2$ is a hydrogen atom or an alkyl group having 1 to 6 carbon atoms, a is an integer of 1 to 6, b is an integer of 0 to 50, c is an integer of 0 to 50, and b+c is at least 5 or bigger), and other As are hydrogen atom(s) or alkyl group(s) having 1 to 6 carbon atoms. The number m is an integer of 1 to 200, and n is an integer of 0 to 50.

In the above-described formula (2). $R^1$ is a side chain on the backbone polysiloxane structure and it is a hydrogen atom or an alkyl group having 1 to 6 carbon atoms. These may be either identical to or different from each other. For example, when all $R^1$s are methyl groups, the structure is a dimethylpolysiloxane structure, and when $R^1$s are a methyl group and a phenyl group, the structure is a methylphenylpolysiloxane structure. A is a location where a polyoxyalkylene group is introduced on the backbone of the polysiloxane structure, and at least one of them is a polyoxyalkylene group represented by the formula: $—(CH_2)_a—(C_2H_4O)_b—(C_3H_6O)_c—R^2$ (in the formula, $R^2$ is a hydrogen atom or an alkyl group having 1 to 6 carbon atoms, a is an integer of 1 to 6, b is an integer of 0 to 50, c is an integer of 0 to 50, and b+c is at least 5 or higher).

In the above-described formula (2), when a portion of As is the above-described polyoxyalkylene group, other As can be a hydrogen atom or an alkyl group having 1 to 6 carbon atoms. For example, when two terminal As are polyoxyalkylene groups, it is an ABA-type polyoxyalkylene-modified silicone. On the other hand, when only the non-terminal As are polyoxyalkylene groups, it is a pendant-type polyoxyalkylene-modified silicone. The polyoxyalkylene group can be any one of the following: polyoxyethylene group, polyoxypropylene group, and polyoxyethylene/polyoxypropylene group. The number of moles of the non-substituted polysiloxane structure m is 1 to 200. The number of moles of the polyoxyalkylene-substituted polysiloxane structure n is 0 to 50. When n is 0, it is necessary that either one or both of the two terminal As are polyoxyalkylene groups.

As such polyoxyalkylene-modified silicone, polyoxyethylene (12 mol) modified dimethylpolysiloxane (pendant-type polyoxyalkylene-modified silicone wherein the side chain methyl group of a linear dimethylpolysiloxane is replaced with a polyoxyethylene (12 mol) group), polyoxyethylene (8 mol) modified dimethylpolysiloxane, and polyoxyethylene (20 mol) modified dimethylpolysiloxane are preferably used. Other examples include an ABA-type polyoxyethylene-methylsiloxane-polyoxyethylene block copolymer.

When polyoxyethylene-modified silicone is used, it is preferable that the percentage of the molecular weight of ethylene oxide in the total molecular weight is 20 to 60%.

The silicone surfactant having HLB of 4 to 12 used in the present invention may be produced by a publicly known method, or commercial products may be used. For example, commercial products include SH3772M (HLB: 6), SH3773M (HLB: 8), and SH3775M (HLB: 5) (all are manufactured by Dow Corning Toray Corporation).

The blending quantity of the vesicle-formable amphiphilic compound is preferably 0.1 mass % or more and more preferably 0.2 mass % or more with respect to the total amount of the composition. If the blending quantity of the vesicle-formable amphiphilic compound is too small, the effect of vesicle formation may not be obtained.

The blending quantity of the vesicle-formable amphiphilic compound is preferably 10 mass % or less and more preferably 5 mass % or less with respect to the total amount of the composition. If the blending quantity of the vesicle-formable amphiphilic compound is too large, the vesicle stability may be poor.

At least part of the vesicle-formable amphiphilic compound is contained as vesicles in the aqueous composition of the present invention. The vesicle formation can be easily carried out by a publicly known method. For example, the vesicles consisting of the vesicle-formable amphiphilic compound can be formed in water by mixing the vesicle-formable amphiphilic compound and water under stirring.

Although the vesicle particle size is not limited in particular, it is normally about 20 to 500 nm and preferably 50 to 200 nm.

As (a) amphiphilic compound, an anionic surfactant and/or a silicone surfactant having HLB of more than 12 is preferably blended other than vesicle-formable amphiphilic compound. By blending an anionic surfactant and/or a silicone surfactant having HLB of more than 12, the vesicle stability especially at a high temperature can be improved. In addition, when a double-layered composition is provided, the layer formation rate (rate of re-separation to two layers after being stirred) can be increased.

As the anionic surfactants, polyoxyethylene alkyl (12-15) ether phosphate, acyl methyl taurate, acyl glutamate are preferably used. Among them, acyl methyl taurate is more preferably used.

Acyl methyl taurate may include, e.g., palm oil fatty acid methyl taurate, palm kernel oil fatty acid methyl taurate, hydrogenated palm kernel oil fatty acid methyl taurate, tallowate methyl taurate, hydrogenated tallowate methyl taurate, caproyl methyl taurate, lauroyl methyl taurate, myristyl methyl taurate, palmitoyl methyl taurate, stearoyl methyl taurate, oleoyl methyl taurate, and cocoyl methyl taurate.

Silicone surfactants having HLB of more than 12 may include, e.g., dimethicone copolyol having HLB of more than 12.

As the dimethicone copolyol having HLB of more than 12, the compound shown in the below-described formula (3) is preferably used.

[Compound 3]

In the above formula (3), p, q, and r, which show the average degrees of polymerization, are p: 5 to 13, q: 4 to 8, and r: 6 to 13.

When anionic surfactant and/or silicone surfactant having HLB of more than 12 is blended, the blending quantity is preferably 0.001 mass % or more and more preferably 0.01 mass % or more with respect to the total amount of the composition. If the blending quantity is too small, the vesicle stability may be poor.

The blending quantity is preferably 1 mass % or less and more preferably 0.1 mass % or less with respect to the total amount of the composition. If the blending quantity is too large, the vesicles may be solubilized.

In addition, in the aqueous composition of the present invention, other amphiphilic compounds may be blended in addition to the above-described amphiphilic compound within the range that the effect of the present patent application is not impaired.

However, if the blending quantity of other amphiphilic compounds is too large, vesicle stability may be impaired. Therefore, the blending quantity of other amphiphilic compounds is preferably 0.1 mass % or less, with respect to the total amount of the composition, and more preferably 0.01 mass % or less, and non-blending is especially preferable.

The blending quantity of amphiphilic compound (a) is preferably 0.1 mass % or more and more preferably 0.2 mass % or more with respect to the total amount of the composition.

The blending quantity is preferably 10 mass % or less and more preferably 5 mass % or less with respect to the total amount of the composition.

((b) Water)

The blending quantity of water is preferably 50 mass % or more and more preferably 70 mass % or more with respect to the total amount of the composition. If the blending quantity is too small, vesicles may not be formed.

The blending quantity is preferably 95 mass % or less and more preferably 90 mass % or less with respect to the total amount of the composition. If the blending quantity is too large, the blending effect of other components may not be obtained.

In the present invention, part of the water may be replaced by aqueous components. The aqueous components are not limited in particular, and they can be used in the range that the vesicle formation and stability are not affected.

Aqueous components may include, e.g., alcohols, sodium chloride, water-soluble polymers, buffer, sequestrant, stabilizer, preservative, UV absorber, antioxidant, and aqueous drugs.

In addition, when vesicle formation is considered, it is preferable to blend alcohol.

Alcohol and the like may include, e.g., ethanol, propylene glycol, dipropylene glycol, and 1,3-butylene glycol.

When alcohol is blended, the blending quantity is preferably 1 mass % or more, with respect to the total amount of the composition, and more preferably 2 mass % or more. The blending quantity is preferably 30 mass % or less and more preferably 25 mass % or less with respect to the total amount of the composition. If the blending quantity of alcohol is out of the above-described range, stable vesicles may not be formed.

Aqueous drugs may include, e.g., vitamins such as inositol, pyridoxine hydrochloride, benzyl nicotinate, amide nicotinate, dl-alpha-tocopherol, magnesium ascorbate phosphate, 2-glucoside ascorbate, potassium dl-alpha-tocopherol, 2-L-ascorbate phosphate diester, pantothenic acid and biotin; anti-inflammatory drug such as allantoin and azulene; skin whitening agent such as arbutin, 4-methoxysalicylate or salts thereof and tranexamic acid or derivatives thereof; astringent such as tannic acid; lysozyme chloride; pyridoxine hydrochloride; and marine collagen.

These aqueous components can suitably be blended in water before the formation of vesicles or before the addition of oil after the preparation of the aqueous composition containing vesicles.

Further, when aqueous agents are blended, it is possible that the vesicle is formed from blending aqueous agents in water and then after by replacing the outer phase, it is also possible that the aqueous composition contains the microcapsule composition in which aqueous agents are present only in the inner phase.

((c) Oil)

As oil (c), oil that separate, when mixed with an amphiphilic compound (a), is preferably used. In the present invention, if the separation into two layers takes place, when component (a) and component (c) are mixed in equal amounts and then allowed to stand at room temperature (25° C.) it is determined that "separation takes place".

If the oil that does not separate when mixed with an amphiphilic compound (a) is used as the oil (c), it may be difficult to obtain the aqueous composition of the present invention, containing vesicles and oil drops.

Such a combination of component (a) and component (c) is not limited in particular. For example, a silicone surfactant having HUB of 4 to 12 can be suitably used as component (a) and hydrocarbon oil can be suitably used as component (c). In this case, it is preferable to add hydrocarbon oil after the preparation of an aqueous solution containing vesicles of the silicone surfactant.

Hydrocarbon oils may include, e.g., volatile hydrocarbon oils such as isododecane, isohexane, isooctane, isohexadecane, and light isoparaffin; and non-volatile hydrocarbon oils such as liquid paraffin and squalane.

Among them, the ratio between the blending quantity of the volatile hydrocarbon oil and the blending quantity of the nonvolatile hydrocarbon oil is preferably 10:4 to 1:0. If the blending quantity of the nonvolatile hydrocarbon oil is too large, the separation of the aqueous layer and the oil layer may be poor in the double-layered composition.

When a silicone surfactant having HLB of 4 to 12 is used as component (a), it is preferable that a silicone oil and/or a polar oil having IOB of 0.05 to 0.8 is contained, as component (c), in addition to hydrocarbon oil. The IOB value of the polar oil can be calculated by a publicly known calculation method based on its structure.

A silicone oil and/or a polar oil having IOB of 0.05 to 0.8 is taken into the bimolecular membrane of the vesicle formed from the silicone surfactant; thus the vesicle can be further stabilized.

The silicone oil is not limited in particular so far as it is an oil component having a polysiloxane structure.

Silicone oils may include, e.g., methyl phenyl silicone such as diphenylsiloxyphenyltrimethicone, trimethylpentaphenyltrisiloxane, diphenyl dimethicone, phenyl trimethicone, dimethylpolysiloxane, methyl hydrogen polysiloxane, octamethyl cyclotetrasiloxane, and decamethylcyclopentasiloxane.

Polar oils having IOB of 0.05 to 0.8 may include e.g., isostearic acid, isopropyl myristate, cetyl octanoate, octyldodecyl myristate, isopropyl palmitate, butyl stearate, hexyl laurate, myristyl myristate, decyl oleate, hexyl decyl dimethyl octanoate, isononyl isononate, cetyl lactate, myristyl lactate, lanolin acetate, isocetyl stearate, isocetyl isostearate, cetyl ethylhexanoate, cholesteryl 12-hydroxystearate, ethylene glycol di2-ethylhexanoate, dipentaerythritol fatty acid ester, N-alkylglycol monoisostearate, neopentyiglycol dicaprate, isostearyl malate, glyceryl di2-heptyl undecanoate, trimethyrol propane tri2-ethylhexanoate, trimethyrol propane triisostearate, pentaerytrityl tetra2-ethyl hexanoate, glyceryl tri2-ethylhexanoate (triethyl hexanoine), trimethyrol propane triisostearate, cetyl isooctanoate, cetyl 2-ethylhexanoate, 2-ethylhexyl palmitate, alkyl (C12-15) benzoate, cetearyl isononanoate, glyceryl tri(caprylate/caprate), butyleneglycol (dicaprylate/caprate), glyceryl trimyristate, glyceride tri2-heptylundecanoate, castor oil fatty acid methyl ester, oleyl oleate, cetosteatyl alcohol, acetoglyceride, 2-heptylundecyl palmitate, diisobutyl adipate, N-lauroyl-L-glutamyl-2-octyldodecyl ester, dig-heptylundecyl adipate, ethyl laurate, di2-ethylhexyl sebacate, 2-hexyldecyl myristate, 2-hexyldecyl palmitate, 2-hexyldecyl adipate, diisopropyl sebacate, di2-ethylhexyl succinate, ethyl acetate, butyl acetate, amyl acetate, triethyl citrate, 2-ethylhexyl p-methoxy cinnamate, tripropyleneglycol dipivalate, and 2-ethylhexyl 2-cyano-3,3-diphenyl acrylate.

When silicone oil and/or polar oil having 1013 of 0.05 to 0.8 is blended, the blending quantity is preferably 0.01 mass % or more and 0.05 mass % or more with respect to the total amount of the composition. If the blending quantity is too small, the effect of blending may not be obtained.

The blending quantity is preferably 1 mass % or less and more preferably 0.2 mass % or less with respect to the total amount of the composition. If the blending quantity is too large, the vesicle stability may not be poor.

Other oil components are not limited in particular and can be used in the range in which the vesicle formation and the stability are not affected.

The blending quantity of oil is preferably 5 mass % or more and more preferably 10 mass % or more with respect to the total amount of the composition. If the blending quantity is too small, the feeling of use such as moist may be inferior.

The blending quantity is preferably 50 mass % or less and more preferably 25 mass % or less with respect to the total amount of the composition. If the blending quantity is too large, the composition may be oily in case.

The production method of the aqueous composition of the present invention comprises: a step of preparing an aqueous solution containing vesicles comprising component (a) by mixing an amphiphilic compound (a) and water (b), and a step of mixing the aqueous solution and the oil (c).

As described above, vesicles can be stabilized in the aqueous composition of the present invention by further blending an anionic surfactant and/or a silicone surfactant having HLB of more than 12.

When an anionic surfactant and/or a silicone surfactant having HLB of more than 12 is blended, it is preferable to blend it after the formation of vesicles. When an anionic surfactant and/or a silicone surfactant having HLB of more than 12 is added before the formation of vesicles, oil (c) may be emulsified due to the surfactant or an ill effect to vesicle stability may result.

When a silicone oil and/or a polar oil having IOB of 0.05 to 0.8 is blended in the aqueous composition of the present invention, it is preferable that it is added and mixed in water before the formation of vesicles. In this case, it is preferable that a silicone oil and/or a polar oil having IOB of 0.05 to 0.8 is added after mixing with alcohol so that it easily dissolves in water.

In this way, a silicone oil and/or a polar oil having IOB of 0.05 to 0.8 can be taken into vesicles (for example, formed from a silicone surfactant having HLB of 4 to 12) and can be present in the bimolecular membrane of the vesicles.

Figure 2:
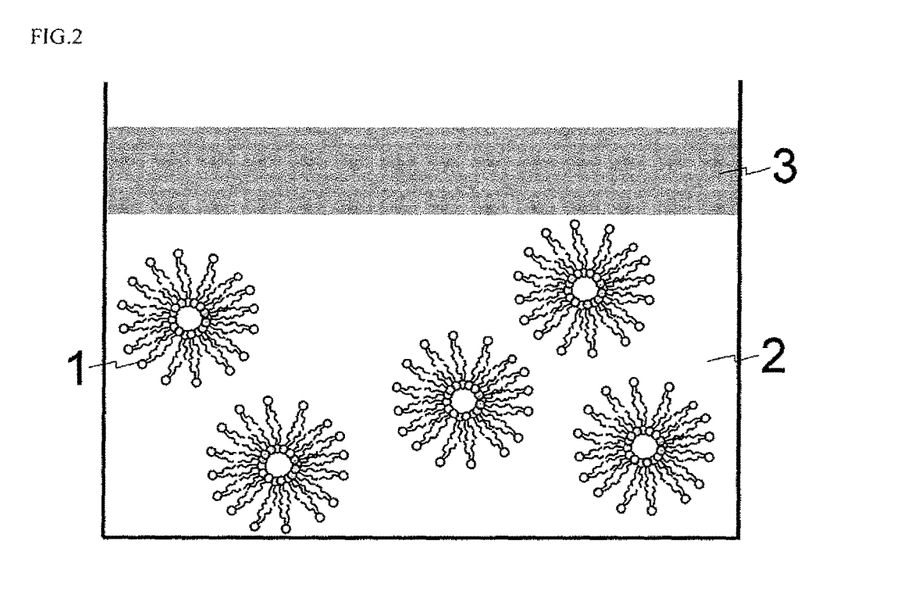
FIG. 2 shows the double-layered composition of the present invention.

The aqueous composition of the present invention can also be provided as a double-layered composition as shown in FIG. 2. That is, the double-layered composition of the present invention is characterized in that the double-layered composition contains an amphiphilic compound (a), water (b), and oil (c); and further comprises an aqueous layer containing component (b) in which vesicles formed from component (a) are present and an oil layer containing component (c).

Double-layered compositions having the colored upper layer and/or the lower layer are provided in many cases, because the appearance thereof is novel and popular. However, when a double-layered composition is applied to cosmetics, an amphiphilic compound cannot be blended so that the compatibility with the skin may be poor. Therefore, it has been difficult to increase repeaters for double-layered cosmetics.

However, an amphiphilic compound is blended in the double-layered composition of the present invention so that the composition can have a good compatibility on the skin.

In addition, the aqueous layer containing vesicles of component (a) formed from the amphiphilic compound looks whity and turbid due to vesicles so that the appearance of the double-layered composition of the present invention can be characteristic even without coloring.

Such a double-layered composition of the present invention can be obtained on standing of the aqueous composition of the present invention for a long period of time.

In order to increase the layer formation rate of the double-layered composition, it is preferable to blend an anionic surfactant and/or a silicone surfactant having HLB of more than 12 into component (a). It is also preferable to blend sodium chloride in component (b). When sodium chloride is blended, a suppressing effect against interface foaming can be obtained.

The aqueous composition and double-layered composition are preferably used as external skin preparations such as cosmetic and medicine. When used as an external skin preparation, the components normally used for the external skin preparation can be blended within the range of the blending quantity in which the vesicle formation and stability are not affected.

When it is used as cosmetics, the cosmetic types are not limited in particular, and wide application is possible. Cosmetics may include, e.g., serum, lotion, milky lotion (emulsion), sunscreen, foundation, cheek, hair liquid, body lotion and so forth.

EXAMPLES

The present invention will be further described in the following examples. However, the invention is not limited to these examples. Unless otherwise specified, the blending quantity of each component will be expressed in mass %.

Prior to illustrating the examples, the methods for the evaluation tests used in the present invention will be explained.

Evaluation (1): Compatibility

Ten expert panelists applied a sample on the face, and the feeling in use when application was evaluated.

A*: 9 panelists or more answered that the compatibility was good.

A: 7 panelists or more and less than 9 panelists answered that the compatibility was good.

B: 5 panelists or more and less than 7 panelists answered that the compatibility was good.

C: Less than 5 panelists answered that the compatibility was good.
Evaluation (2): Moist
  Ten expert panelists applied a sample on the face, and the feeling in use immediately after application was evaluated.
A*: 9 panelists or more answered that the skin was moist.
A: 7 panelists or more and less than 9 panelists answered that the skin was moist.
B: 5 panelists or more and less than 7 panelists answered that the skin was moist.
C: Less than 5 panelists answered that the skin was moist.
Evaluation (3): Non-Stickiness
  Ten expert panelists applied a sample on the face, and the feeling in use immediately after application was evaluated.
A*: 9 panelists or more answered that the skin was not sticky.
A: 7 panelists or more and less than 9 panelists answered that the skin was not sticky.
B: 5 panelists or more and less than 7 panelists answered that the skin was not sticky.
C: Less than 5 panelists answered that the skin was not sticky.
Evaluation (4): Non-Oiliness
  Ten expert panelists applied a sample on the face, and the feeling in use immediately after application was evaluated.
A*: 9 panelists or more answered that the skin was not oily.
A: 7 panelists or more and less than 9 panelists answered that the skin was not oily.
B: 5 panelists or more and less than 7 panelists answered that the skin was not oily.
C: Less than 5 panelists answered that the skin was not oily.
Evaluation (5): Appearance
  The appearance at ordinary temperature (25° C.) it was observed after 24 hours from sample production. When the appearance was translucent, it was determined as "vesicles", and when the appearance was cloudy, it was determined as "emulsion".
Evaluation (6): Vesicle Stability
  At first, the L value (initial value) of the aqueous solution containing vesicles (only the aqueous layer) was measured. After the elapse of 4 weeks, the L value was measured again. The vesicle stability was evaluated by the change of the L value.
A*: The change from the initial value was within ±5.
A: The change from the initial value was within ±10.
B: The change from the initial value was within ±15.
C: The change from the initial value exceeded ±15.
Evaluation (7): Separation Property
  The time necessary for separation after sample preparation was measured.
(Evaluation Criteria)
A*: It was within 8 hours.
A: It was within 16 hours.
B: It was within 24 hours.
C: It exceeded 24 hours.

At first, the present inventor and associates prepared a sample of silicone vesicle-containing composition, which has been well known in the past (Test Example 1-1). By varying the kinds of oil and the blending quantity in this sample, the compositions with blending compositions shown in below Table 1 were produced by the below-described production method A. Then, each sample was evaluated by the above-described evaluation methods for evaluation items (1) to (5). The result is shown in Table 1.
(Production Method A)
  An amphiphilic compound, water, and aqueous components were stirred, and then oil was added and stirred.

TABLE 1

|  | Test Example | | |
|---|---|---|---|
|  | 1-1 | 1-2 | 1-3 |
| POE(12) dimethyl polysiloxane (*1) | 0.5 | 0.5 | 0.5 |
| Ion exchanged water | balance | balance | balance |
| Ethanol | 2.5 | 2.5 | 2.5 |
| Methylphenylsiloxane (*2) | 0.1 | 14 | — |
| Isododecane | — | — | 14 |
| Mixing state (*3) | dissolution | dissolution | separation |
| Evaluation (1): Compatibility | A* | A | A* |
| Evaluation (2): Moist | B | A* | A* |
| Evaluation (3): Non-stickiness | A* | B | A* |
| Evaluation (4): Non-oiliness | A* | B | A* |
| Evaluation (5): Appearance | Vesicles (L value: 93) | Emulsion | Vesicles + oil (2 phases) |

(*1): SH3773M (manufactured by Dow Corning Toray Corporation (HLB = 8))
(*2): KF-56 (manufactured by Shin-Etsu Chemical Co., Ltd.)
(*3): The state at room temperature (25° C.) when the amphiphilic compound (POE(12) dimethylpolysiloxane) and oil (methylphenylsiloxane or isododecane) were mixed at a ratio of 1:1.

According to Test Example 1-2, when the quantity of oil blended into the conventional silicone vesicle-containing composition is increased, an emulsion was found to be caused because it becomes difficult that the amphiphilic compound is taken into the silicone vesicles.

Further, according to Test Example 1-3, a stable composition was found to be obtained if isododecane that is an oil separating from the vesicle-formable amphiphilic compound is used despite blending a large amount of oil.

As a result of these investigations, it was found that in the vesicle-containing aqueous composition containing an amphiphilic compound (a) and water (b), oil that separates from vesicle-formable amphiphilic compound (a) is preferably used as an oil (c). If such oil (c) is included, oil drops can be stably contained in the vesicle-containing composition.

For example, the combination of the above-described component (a) and component (c) includes a combination of a silicone surfactant having HLB of 4 to 12 as component (a) and a hydrocarbon oil as component (c).

Such an aqueous composition containing oil drops and vesicles according to the present invention, which is different from the conventional vesicle-containing composition in which a large amount of oil cannot be blended, can be blended with a large amount of oil so that the moist feeling when applied on the skin is excellent. In addition, the skin compatibility is also excellent because vesicles are contained.

After a long period of time, even if the composition of the present invention separate to two layers including the aqueous layer (containing vesicles) and the oil layer, it has been clarified that an aqueous composition containing vesicles and oil drops could be easily obtained by shaking it.

Subsequently, the present inventor and associates produced aqueous compositions with the blending compositions shown in below Table 2, wherein component (a) and/or component (b) was added to the aqueous composition of the present invention (Test Example 1-3), by the above-described production method A. Then, each sample was evaluated by the above-described evaluation methods for evaluation items (6) and (7). The result is shown in Table 2.

TABLE 2

| | | Test Example | | | | |
|---|---|---|---|---|---|---|
| | | 1-3 | 2-1 | 2-2 | 2-3 | 2-4 |
| (a) | POE(12) dimethyl polysiloxane (*1) | 0.5 | 0.5 | 0.5 | 0.5 | 0.5 |
| | Dimethicone copolyol (*4) | — | — | 0.05 | 0.05 | 0.05 |

TABLE 2-continued

| | | Test Example | | | | |
|---|---|---|---|---|---|---|
| | | 1-3 | 2-1 | 2-2 | 2-3 | 2-4 |
| (b) | Ion exchanged water | balance | balance | balance | balance | balance |
| | Ethanol | 2.5 | 2.5 | 2.5 | 2.5 | 2.5 |
| | Sodium chloride | — | 1 | — | 1 | 1 |
| | Dipropylene glycol | — | — | — | — | 6 |
| (c) | Isododecane | 14 | 14 | 14 | 14 | 14 |
| | Evaluation (6): Vesicle stability | B | B | A* | A* | A* |
| | Evaluation (7): Separation property | B | A* | A | A* | A* |

*4: Silwet 10-E (manufactured by Dow Corning Toray Corporation (HLB = about 14))

According to Table 2, the aqueous composition of the present invention was found to separate into two layers on standing. Therefore, the composition of the present invention can be provided as a double-layered composition.

It was also found from Table 2 that when a double-layered composition is produced, it is preferable to blend dimethicone copolyol and/or sodium chloride. In addition, the sample, in which dimethicone copolyol that is a silicone surfactant having HLB of more than 12 is blended, was also excellent in vesicle stability.

It was also found from Test Example 2-4 that a double-layered composition excellent in the feeling in use could be obtained even when water is replaced with a moisturizer (dipropylene glycol).

Next, the present inventor and associates investigated the kinds of component (b) and component (c) and their blending quantities in the aqueous composition of the present invention (double-layered composition). The present inventor and associates prepared aqueous compositions (Test Examples 3-1 to 3-4) of blending compositions shown in below Table 3 by the below-described production method B that is a publicly known production method of vesicle-containing compositions. Then, each sample was evaluated by the above-described evaluation methods for evaluation items (2), (6) and (7). The result is shown in Table 3.

(Production Method B)

A vesicle-containing composition was prepared by mixing under stirring, component (a), component (b), and silicone oil (methylphenylpolysiloxane). The mixed oil other than silicone oil was added to the vesicle-containing composition and was mixed.

TABLE 3

| | | Test Example | | | | |
|---|---|---|---|---|---|---|
| | | 2-4 | 3-1 | 3-2 | 3-3 | 3-4 |
| (a) | POE(12) dimethyl polysiloxane (*1) | 0.5 | 0.5 | 0.5 | 0.5 | 0.5 |
| | Dimethicone copolyol (*4) | 0.05 | 0.05 | 0.05 | 0.05 | 0.05 |
| (b) | Ion exchanged water | balance | balance | balance | balance | balance |
| | Ethanol | 2.5 | 2.5 | 2.5 | 2.5 | 2.5 |
| | Sodium chloride | 1 | 1 | 1 | 1 | 1 |
| | Dipropylene glycol | 6 | 6 | 6 | 6 | 6 |
| | Glycerin | — | — | 14 | 14 | 14 |
| (c) | Isododecane | 14 | 14 | 10 | 10 | 0 |
| | Synthetic isoparaffin | — | — | 4 | 0 | 0 |
| | Liquid paraffin | — | — | 0 | 4 | 14 |
| | Methylphenylsiloxane (*2) | — | 0.1 | 0.1 | 0.1 | 0.1 |
| | Evaluation (2): Moist | A* | A* | A* | A* | A* |
| | Evaluation (6): Vesicle stability | A* | A* | A* | A* | A* |
| | Evaluation (7): Separation property | A* | A* | A* | A | B |

Test Example 3-1 in which a small amount of methylphenylpolysiloxane was blended as the oil was better in moistness and vesicle stability than Test Example 2-4.

In addition, even when part of isododecane is replaced by synthetic isoparaffin or liquid paraffin, which is the oil that separates from the vesicle-formable amphiphilic compound (POE(12)dimethylpolysiloxane), a double-layered composition excellent in the feeling in use was found to be obtained (Test Examples 3-2 and 3-3).

However, as shown in Test Example 3-4, if the blending quantity of liquid paraffin is increased, the separation between the aqueous layer and the oil layer was found to become poor.

As a result of these investigations, in the aqueous composition of the present invention containing a silicone surfactant having HLB of 4 to 12 as component (a) and hydrocarbon oil as component (c), the ratio between the blending quantity of volatile hydrocarbon oil represented by isododecane and the blending quantity of non-volatile hydrocarbon oil represented by liquid paraffin is preferably 10:4 to 1:0.

Next, the present inventor and associates prepared aqueous compositions of blending compositions shown in below Table 4 by the above-described production method B or the below-described production method C or D. Then, each sample was evaluated by the above-described evaluation methods for evaluation items (1) to (5). The result is shown in Table 4.

Figure 3:
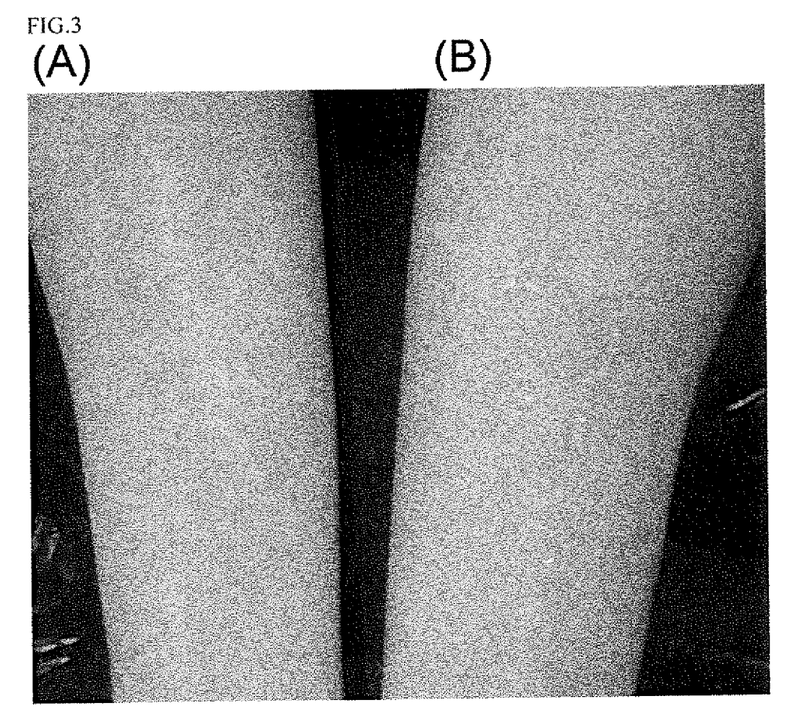
FIG. 3 shows (A) photo when the aqueous composition of the present invention (shaken double-layered cosmetic of the present invention; Test Example 4-1) was applied on the skin and (B) photo when the conventional double-layered cosmetic (Test Example 4-3) was shaken and applied on the skin.

In addition, the sample of Test Example 4-1 (aqueous composition of the present invention) and the sample of Test Example 4-3 (conventional double-layered cosmetic) were sufficiently shaken, they were applied to left and right arms of a subject, and the taken photos are shown in FIGS. 3(A) and 3(B), respectively.

(Production Method C)

Component (a), component (b), and methylphenylpolysiloxane were stirred and mixed to prepare a vesicle-containing composition. To the composition, isododecane was added and mixed. Then, the stirring was carried out with a homomixer until it became homogeneous.

(Production Method D)

Isododecane was added after components (b) were stirred, and the mixture was stirred.

TABLE 4

|     |     | Test Example | | |
| --- | --- | --- | --- | --- |
|     |     | 4-1 | 4-2 | 4-3 |
| (a) | POE(12) dimethyl polysiloxane (*1) | 0.5 | 0.5 | — |
|     | Dimethicone copolyol (*4) | 0.05 | 0.05 | — |
| (b) | Ion exchanged water | balance | balance | balance |
|     | Sodium chloride | 1 | 1 | 1 |
|     | Dipropylene glycol | 6 | 6 | 6 |
|     | Glycerin | 14 | 14 | 14 |
|     | 1,3-butylene glycol | 0.9 | 0.9 | 0.9 |
|     | Ethanol | 2.6 | 2.6 | 2.6 |
|     | Xanthane gum | 0.04 | 0.04 | 0.04 |
|     | Phenoxyethanol | 0.5 | 0.5 | 0.5 |
|     | Sodium citrate | 0.07 | 0.07 | 0.07 |
|     | Citric acid | 0.02 | 0.02 | 0.02 |
|     | Disodium ethylenediaminetetraacetate solution | proper quantity | proper quantity | proper quantity |
| (c) | Isododecane | 14 | 14 | 14 |
|     | Methylphenylsiloxane (*2) | 0.09 | 0.09 | — |
|     | Production method | B | C | D |
|     | Evaluation (1): Compatibility | A* | A | B |
|     | Evaluation (2): Moist | A* | A* | B |
|     | Evaluation (3): Non-stickiness | A* | B | A |
|     | Evaluation (4): Non-oiliness | A* | B | A |
|     | Evaluation (5): Appearance | Vesicles + Oil drops | Emulsion | 2 phases (Water phase + Oil phase) |

According to Table 4, if the production was not conducted by the method for obtaining a vesicle-containing composition, an emulsion was generated (Test Example 4-2) despite the same compositions, and no separation to two layers was found to take place.

When an amphiphilic compound (a) was not blended, a double-layered composition could be easily obtained (Test Example 4-3).

According to FIG. 3(B), however, the skin compatibility was poor in Test Example 4-3. On the other hand, as shown in FIG. 3(A), the aqueous composition of the present invention (Test Example 4-1) was found to be good in skin compatibility.

According to Table 4, the aqueous composition of the present invention was found to be excellent in the feeling in use compared with the conventional emulsion and the double-layered composition.

Next, the present inventor and associates investigated the blending quantity of oil. The present inventor and associates prepared compositions of blending compositions shown in below Table 5, wherein the blending quantities of oils were changed, by the above-described production method B. Then, each sample was evaluated by the above-described evaluation methods for evaluation items (1) to (4). The result is shown in Table 5.

TABLE 5

|     | Test Example | 5-1 | 5-2 | 5-3 | 5-4 | 5-5 | 5-6 |
| --- | --- | --- | --- | --- | --- | --- | --- |
| (a) | POE(12) dimethyl polysiloxane (*1) | 0.5 | 0.5 | 0.5 | 0.5 | 0.5 | 0.5 |
|     | Dimethicone copolyol (*4) | 0.05 | 0.05 | 0.05 | 0.05 | 0.05 | 0.05 |

TABLE 5-continued

|     | Test Example | 5-1 | 5-2 | 5-3 | 5-4 | 5-5 | 5-6 |
| --- | --- | --- | --- | --- | --- | --- | --- |
| (b) | Ion exchanged water | balance | balance | balance | balance | balance | balance |
|     | Ethanol | 2.5 | 2.5 | 2.5 | 2.5 | 2.5 | 2.5 |
|     | Sodium chloride | 1 | 1 | 1 | 1 | 1 | 1 |
|     | Dipropylene glycol | 6 | 6 | 6 | 6 | 6 | 6 |
|     | Glycerin | 14 | 14 | 14 | 14 | 14 | 14 |
| (c) | Isododecane | 0.04 | 0.4 | 2 | 4 | 8 | 22 |
|     | Synthetic isoparaffin | 0.05 | 0.5 | 2.5 | 5 | 10 | 27 |
|     | Liquid paraffin | 0.01 | 0.1 | 0.5 | 1 | 2 | 3 |
|     | Methylphenylsiloxane (*2) | 0.001 | 0.01 | 0.05 | 0.1 | 0.2 | 0.5 |
| Evaluation (1): Compatibility | | A* | A* | A* | A* | A* | A* |
| Evaluation (2): Moist | | B | B | A | A* | A* | A* |
| Evaluation (3): Non-stickiness | | A* | A* | A* | A* | A | B |
| Evaluation (4): Non-oiliness | | A* | A* | A* | A* | A* | B |

According to Table 5, when the blending quantity of oil (c) in the aqueous composition is too small, it was difficult to feel moistness. When the blending quantity of oil (c) in the aqueous composition is too large, oiliness was easily felt.

Accordingly, in the aqueous composition of the present invention, the blending quantity of oil (c) is preferably 5 to 50 mass %.

Hereinafter, formulation examples of the aqueous composition and double-layered composition of the present invention will be listed. The present invention is not limited to these examples.

Formulation Example 1: Serum/Double-Layered Serum (If shaken on use, it turns to a serum. A double-layered serum is obtained in 8 hours after shaking.)

| Formulation Example 1: Serum/Double-layered serum (If shaken on use, it turns to a serum. A double layered serum is obtained in 8 hours after shaking.) | |
| --- | --- |
| POE (12) dimethylpolysiloxane | 0.6 |
| Dimethicone copolyol | 0.04 |
| Water | balance |
| Glycerin | 14 |
| Ethanol | 2.5 |
| Dipropylene glycol | 6 |
| 1,3-butylene glycol | 1 |
| Sodium chloride | 0.8 |
| Phenoxyethanol | 0.5 |
| Sodium citrate | 0.07 |
| Citric acid | 0.02 |
| Sodium pyrosulfate | 0.01 |
| Disodium edetate dihydrate | 0.01 |
| Synthetic isoparaffin | 7 |
| Isododecane | 6 |
| Liquid paraffin | 1 |
| Methyl phenyl polysiloxane | 0.08 |
| Perfume | proper quantity |
| Formulation Example 2: Serum/Double-layered serum | |
| Water | balance |
| Ethanol | 8.0 |
| Glycerin | 0.8 |
| PEG/PPG-17/4 dimethylether | 4.0 |
| PEG-10 hydrogeneted castor oil | 2.0 |
| Phenoxyethanol | 0.4 |
| Disodium edetate dihydrate | 0.04 |
| Xylitol | 2.5 |
| Xanthane gum | 0.12 |
| Decamethyltetrasiloxane | 20.0 |

DESCRIPTION OF THE REFERENCES

1: (a) An amphiphilic compound
2: (b) Water
3: (c) Oil

What is claimed is:

1. An aqueous composition, comprising:
    (a) an amphiphilic component comprising a vesicle-forming amphiphilic compound,
    (b) an aqueous component comprising one or more alcohols and water, and
    (c) an oil component, comprising a hydrocarbon oil, which separates from the aqueous component when mixed with a mixture of component (a) and component (b),
    wherein
        said vesicle-forming amphiphilic compound comprises a silicone surfactant having HLB of 4 to 12, and
        component (b) further comprises vesicles formed from component (a) and oil drops comprising component (c), and
    wherein the aqueous composition is obtained by a process comprising the steps of preparing the mixture of component (a) and component (b), and subsequently combining the mixture of component (a) and component (b) with the hydrocarbon oil.

2. The aqueous composition, according to claim 1, wherein the amphiphilic component further comprises a vesicle-forming amphiphilic compound selected from the group consisting of sugar fatty acid ester, polyoxyethylene hydrogenated castor oil derivative, acyl-amino acid metal salt and phospholipid.

3. The aqueous composition, according to claim 1, wherein the component (a) further comprises an anionic surfactant and/or a silicone surfactant having HLB of more than 12.

4. The aqueous composition, according to claim 3, wherein the component (b) further comprises:
    vesicles formed from a silicone surfactant having HLB of 4 to 12; and
    oil drops containing hydrocarbon oil;
    wherein said anionic surfactant and/or silicone surfactant having HLB of more than 12 adheres to the surface of said vesicles.

5. The aqueous composition, according to claim 1, wherein the component (c) further comprises a silicone oil and/or a polar oil having IOB of 0.05 to 0.8, and wherein the aqueous composition is obtained by a process comprising the steps of preparing a mixture of component (a), component (b) and the silicone oil and/or the polar oil, and subsequently combining the mixture of component (a) and component (b) and the silicone oil and/or the polar oil with the hydrocarbon oil.

6. The aqueous composition, according to claim 5, wherein the component (b) further comprises:
    oil drops including vesicles formed from a silicone surfactant having HLB of 4 to 12 and hydrocarbon oil; and
    a bimolecular membrane of said vesicles including the silicone oil and/or the polar oil having IOB of 0.05 to 0.8.

7. The aqueous composition, according to claim 1, wherein said alcohols are selected from the group consisting of ethanol, propylene glycol, dipropylene glycol, and 1,3-butylene glycol.

8. A production method of an aqueous composition, comprising:
    a step of mixing a silicone surfactant having HLB of 4 to 12 (a) and an aqueous component comprising one or more alcohols and water (b),
    a step of preparing an aqueous solution containing vesicles comprising component (a), and
    a step of mixing said aqueous solution and an amount of hydrocarbon oil (c) producing a composition having 5% to 50% by mass hydrocarbon oil, with respect to the total mass of the composition.

9. The production method according to claim 8, further comprising a step of adding a silicone oil and/or a polar oil having IOB of 0.05 to 0.8 after mixing component (a) and component (b).

10. A double-layered composition, comprising:
    (a) an amphiphilic component comprising a vesicle-forming amphiphilic compound,
    (b) an aqueous layer comprising one or more alcohols and water, and
    (c) 5% to 50% by mass, with respect to the total mass of the composition, of an oil layer, comprising a hydrocarbon oil, which separates from the aqueous component when mixed with a mixture of component (a) and component (b),
    wherein
        the vesicle-forming amphiphilic compound comprises a silicone surfactant having HLB of 4 to 12, and
        the aqueous layer (b) comprises vesicles formed from component (a), and
    wherein the double-layered composition is obtained by a process comprising the steps of preparing the mixture of component (a) and component (b), and subsequently combining the mixture of component (a) and component (b) with the hydrocarbon oil.

11. The double-layered composition, according to claim 10, wherein said amphiphilic component further comprises a vesicle-forming amphiphilic compound selected from the group consisting of sugar fatty acid ester, polyoxyethylene hydrogenated castor oil derivative, acyl-amino acid metal salt and phospholipid, and a silicone surfactant having HLB of 4 to 12.

12. The double-layered composition, according to claim 10, wherein said component (a) further comprises an anionic surfactant and/or a silicone surfactant having HLB of more than 12.

13. The double-layered composition, according to claim 12, wherein said double-layered composition further comprises:
    an aqueous layer comprising vesicles formed from a silicone surfactant having HLB of 4 to 12 and
    an oil layer comprising hydrocarbon oil,
    wherein said anionic surfactant and/or said silicone surfactant having HLB of more than 12 adheres on the surface of said vesicles.

14. The double-layered composition, according to claim 10, wherein said component (c) further comprises a silicone oil and/or a polar oil having IOB of 0.05 to 0.8.

15. The double-layered composition, according to claim 14, wherein said double-layered composition comprises:
    an aqueous layer comprising vesicles formed from a silicone surfactant having HLB of 4 to 12 and
    an oil layer comprising hydrocarbon oil,
    wherein a vesicle membrane bilayer formed from the silicone surfactant comprises a silicone oil and/or a polar oil having IOB of 0.05 to 0.8 within the bilayer.

16. The double-layered composition, according to claim 10, wherein said component (c) further comprises sodium chloride.

17. The double-layered composition, according to claim 10, wherein said alcohols are selected from the group consisting of ethanol, propylene glycol, dipropylene glycol, and 1,3-butylene glycol.

* * * * *